US011826025B2

United States Patent
Oishi et al.

(10) Patent No.: US 11,826,025 B2
(45) Date of Patent: Nov. 28, 2023

(54) IMAGING MODULE

(71) Applicant: Fujikura Ltd., Tokyo (JP)

(72) Inventors: Wataru Oishi, Sakura (JP); Yoshinobu Numasawa, Sakura (JP)

(73) Assignee: Fujikura Ltd., Tokyo (JP)

( * ) Notice: Subject to any disclaimer, the term of this patent is extended or adjusted under 35 U.S.C. 154(b) by 424 days.

(21) Appl. No.: 17/292,594

(22) PCT Filed: Dec. 3, 2019

(86) PCT No.: PCT/JP2019/047272
§ 371 (c)(1),
(2) Date: May 10, 2021

(87) PCT Pub. No.: WO2020/137384
PCT Pub. Date: Jul. 2, 2020

(65) Prior Publication Data
US 2021/0409620 A1    Dec. 30, 2021

(30) Foreign Application Priority Data

Dec. 26, 2018  (JP) ................. 2018-242053

(51) Int. Cl.
*H01L 23/498* (2006.01)
*H04N 23/54* (2023.01)
(Continued)

(52) U.S. Cl.
CPC .......... *A61B 1/051* (2013.01); *A61B 1/00114* (2013.01); *H01L 23/49827* (2013.01);
(Continued)

(58) Field of Classification Search
CPC .... A61B 1/051; A61B 1/00114; H04N 23/54; H04N 25/00; H04N 23/52; H01L 23/49827; H01L 23/49894
(Continued)

(56) References Cited

FOREIGN PATENT DOCUMENTS

| JP | S61-163315 A | 7/1986 |
| JP | S63-108314 A | 5/1988 |

(Continued)

OTHER PUBLICATIONS

English translation of the International Search Report issued in corresponding International Application No. PCT/JP2019/047272 dated Jan. 28, 2020 (2 pages).

*Primary Examiner* — Joel W Fosselman
(74) *Attorney, Agent, or Firm* — Osha Bergman Watanabe & Burton LLP

(57) ABSTRACT

An imaging module of the invention includes an image-sensing device that has a light-receiving face, a substrate, a signal cable including a conductor, and a resin mold. A wiring of the substrate includes an electrode terminal and a cable terminal. The image-sensing device electrode is electrically connected to the electrode terminal via solder. The conductor is electrically connected to the cable terminal via solder. The resin mold coats the electrode surface, the cable terminal, the conductor, and the solder. On a plane of projection of the image-sensing device when viewed in a direction from the image-sensing device to the signal cable, the substrate, the resin mold, and the signal cable are disposed inside an outline of the image-sensing device.

6 Claims, 5 Drawing Sheets

(51) Int. Cl.
*A61B 1/05* (2006.01)
*A61B 1/00* (2006.01)
*H04N 25/00* (2023.01)

(52) U.S. Cl.
CPC ....... *H01L 23/49894* (2013.01); *H04N 23/54* (2023.01); *H04N 25/00* (2023.01)

(58) Field of Classification Search
USPC .......................................... 348/294
See application file for complete search history.

(56) References Cited

FOREIGN PATENT DOCUMENTS

| | | |
|---|---|---|
| JP | H05-220107 A | 8/1993 |
| JP | H06-070207 A | 3/1994 |
| JP | H08-271809 A | 10/1996 |
| JP | H10-050969 A | 2/1998 |
| JP | H11-076156 A | 3/1999 |
| JP | 2000-199863 A | 7/2000 |
| JP | 2006-061327 A | 3/2006 |
| JP | 2011-166080 A | 8/2011 |
| JP | 2011-200398 A | 10/2011 |
| JP | 2014-015084 A | 1/2014 |
| JP | 2014-110847 A | 6/2014 |
| JP | 2017-099856 A | 6/2017 |
| JP | 2018-089066 A | 6/2018 |
| WO | 2016/042804 A1 | 3/2016 |
| WO | WO-2019193911 A1 * | 10/2019 ............. A61B 1/051 |

* cited by examiner

IMAGING MODULE

CROSS-REFERENCE TO RELATED APPLICATIONS

This application claims priority from Japanese Patent Application No. 2018-242053 filed on Dec. 26, 2018, the contents of which are incorporated herein by reference in their entirety.

TECHNICAL FIELD

The present invention relates to an imaging module.

BACKGROUND

Conventionally, a small solid-state imaging device that is applied to an electronic endoscope or the like is known (for example, refer to Patent Document 1). Such solid-state imaging device includes a T-shaped multilayer ceramic substrate such that a perpendicular substrate having a solid-state image sensing device mounted thereon and a horizontal substrate provided with a terminal part or wirings is disposed so as to be orthogonal to each other. The perpendicular substrate and the horizontal substrate each have bonding pads, the bonding pads of both the substrates are electrically connected to each other by solder, and the perpendicular substrate and the horizontal substrate are fixed by the solder. Additionally, on the horizontal substrate, the terminal parts are electrically connected to an electronic component and a signal cable by the solder.

PATENT LITERATURE

[Patent Document 1] Japanese Unexamined Patent Application, First Publication No. 2000-199863

In the aforementioned solid-state imaging device, the bonding pad of the perpendicular substrate and the horizontal substrate are connected to each other only by the solder. Furthermore, the electronic component or the signal cable are connected to the terminal part of the horizontal substrate only be the solder. In such configuration, joint strength is not sufficiently ensured, peeling easily occurs between the bonding pads of both substrates, and furthermore the electronic component or the signal cable is easily peeled from the terminal part. Moreover, since the solder is exposed, it is difficult to ensure electrical insulation.

SUMMARY

One or more embodiments of the invention provide an imaging module that achieves reduction in diameter thereof, ensures electrical insulation, and can improve joint strength between wirings or electrodes and terminals which are formed on a substrate.

An imaging module according to one or more embodiments of the invention, includes: an image-sensing device that has a light-receiving face and an electrode surface located on the opposite side of the light-receiving face, and includes a plurality of image-sensing device electrodes that are formed on the electrode surface; a substrate that has a first surface, a second surface opposite to the first surface, a first end face that faces the electrode surface located between two image-sensing device electrodes adjacent to each other, includes a wiring that is formed on the first surface and the second surface, and serves an insulating member; a signal cable that includes a conductor that is electrically connected to the image-sensing device via the wiring of the substrate; and a resin mold that coats at least one of the first surface and the second surface on the substrate, wherein the wiring of the substrate includes an electrode terminal and a cable terminal, the image-sensing device electrode is electrically connected to the electrode terminal via solder, the conductor is electrically connected to the cable terminal via solder, the resin mold coats the electrode surface, the cable terminal, the conductor, and the solder, on a plane of projection of the image-sensing device when viewed in a direction from the image-sensing device to the signal cable, the substrate, the resin mold, and the signal cable are disposed inside an outline of the image-sensing device.

Since the imaging module of one or more embodiments of the invention includes the resin mold that coats the electrode surface, the cable terminal, the solder, and the signal cable, it is possible to ensure electrical insulation, it is possible to improve joint strength between the image-sensing device electrode and the wiring, and it is possible to improve joint strength between the cable terminal and the signal cable.

Furthermore, since the substrate, the resin mold, and the signal cable are disposed inside the outline of the image-sensing device on a plane of projection of the image-sensing device when viewed in a direction from the image-sensing device to the signal cable, the size of the imaging module can be on the plane of projection of the image-sensing device, and it is possible to achieve reduction in diameter of the imaging module.

In the imaging module according to one or more embodiments of the invention, the substrate has a side surface that is connected to the first surface and the second surface via a corner, the side surface extends in a direction from the image-sensing device to the signal cable, and the side surface may not be coated with the resin mold.

In the imaging module according to one or more embodiments of the invention, the substrate has a second end face opposite to the first end face, and the resin mold may coat the second end face.

In the imaging module according to one or more embodiments of the invention, the resin mold coats both surfaces of the first surface and the second surface, the resin mold includes a first resin portion that coats the first surface and a second resin portion that coats the second surface, and the first resin portion may be connected to the second resin portion on the second end face.

In the imaging module according to one or more embodiments of the invention, the resin mold may be formed in a fillet shape having a curved surface extending from a corner of the electrode surface to an outer coating end of the signal cable.

In the imaging module according to one or more embodiments of the invention, the signal cable is a coaxial cable including an internal conductor and an external conductor located outside the internal conductor, the cable terminal of the substrate includes: an internal conductor terminal that is electrically connected to the internal conductor via the solder; and an external conductor terminal electrically connected to the external conductor via the solder, and the resin mold may coat an entirety of the image-sensing device electrode, the internal conductor, the external conductor, the solder, the internal conductor terminal, and the external conductor terminal.

Effects of the Invention

As described above, it is possible to provide an imaging module that achieves reduction in diameter thereof, ensures electrical insulation, and can improve joint strength between wirings or electrodes and terminals which are formed on a substrate, according to one or more embodiments.

DETAILED DESCRIPTION

Figure 1:
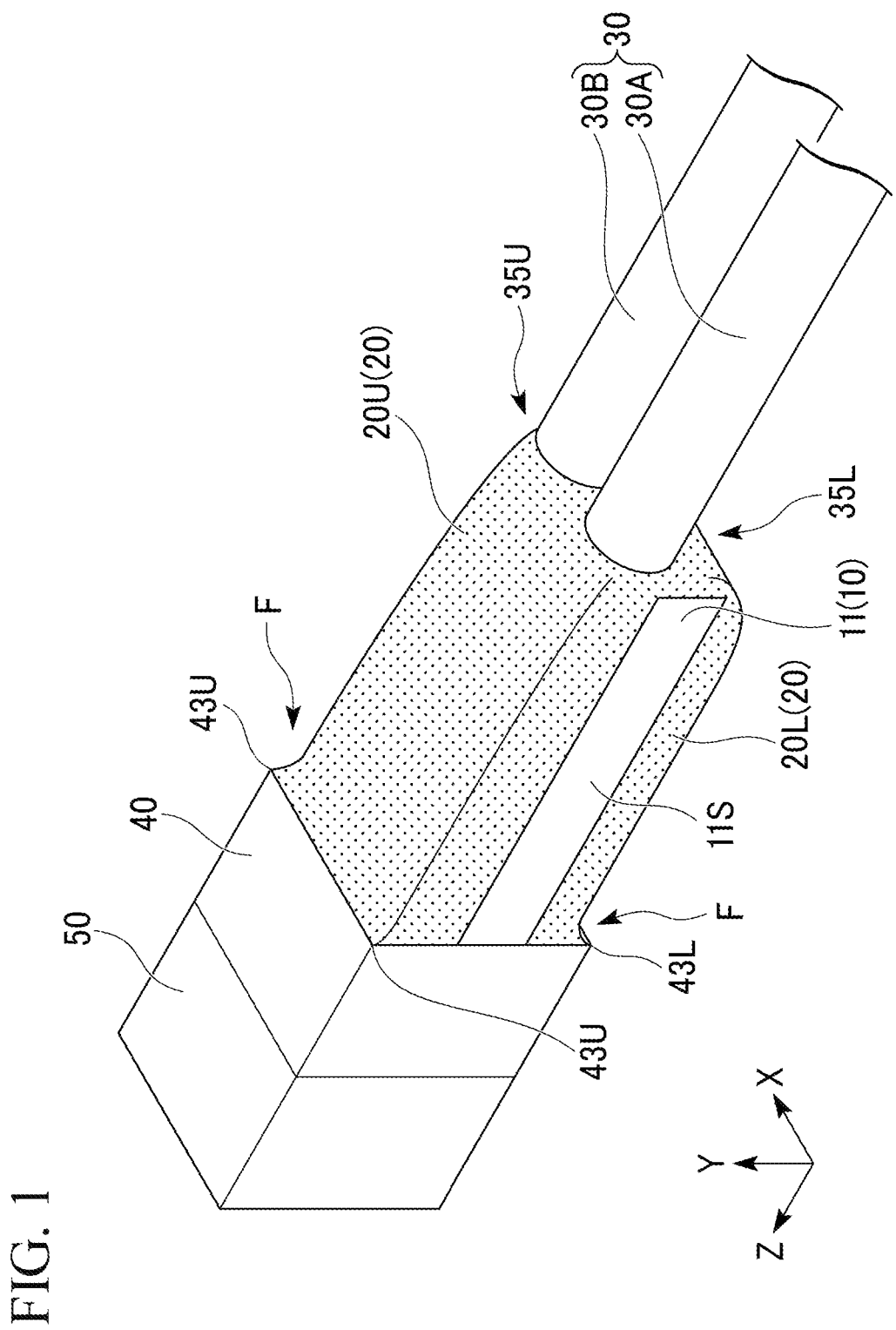
FIG. 1 is a perspective view showing a schematic configuration of an imaging module according to one or more embodiments of the invention.

Hereinafter, embodiments of the invention will be described with reference to drawings.

In the drawings showing embodiments of the invention, in order for the respective components to be of understandable size in the drawings, the dimensions and the proportions of the components are modified as needed compared with the real components.

(Imaging Module)

Figure 2:
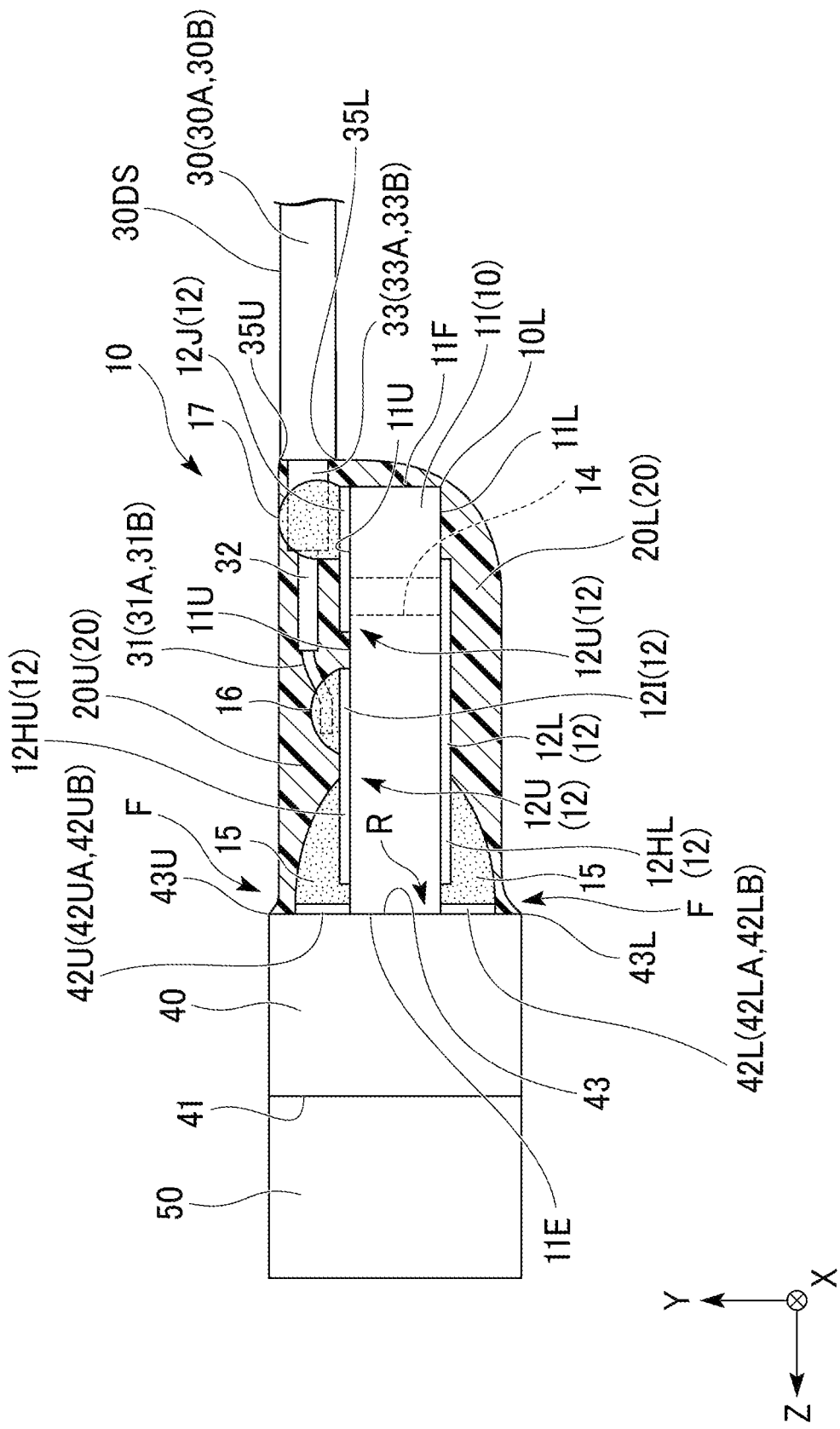
FIG. 2 is a cross-sectional view showing the schematic configuration of the imaging module according to one or more embodiments of the invention.
Figure 3:
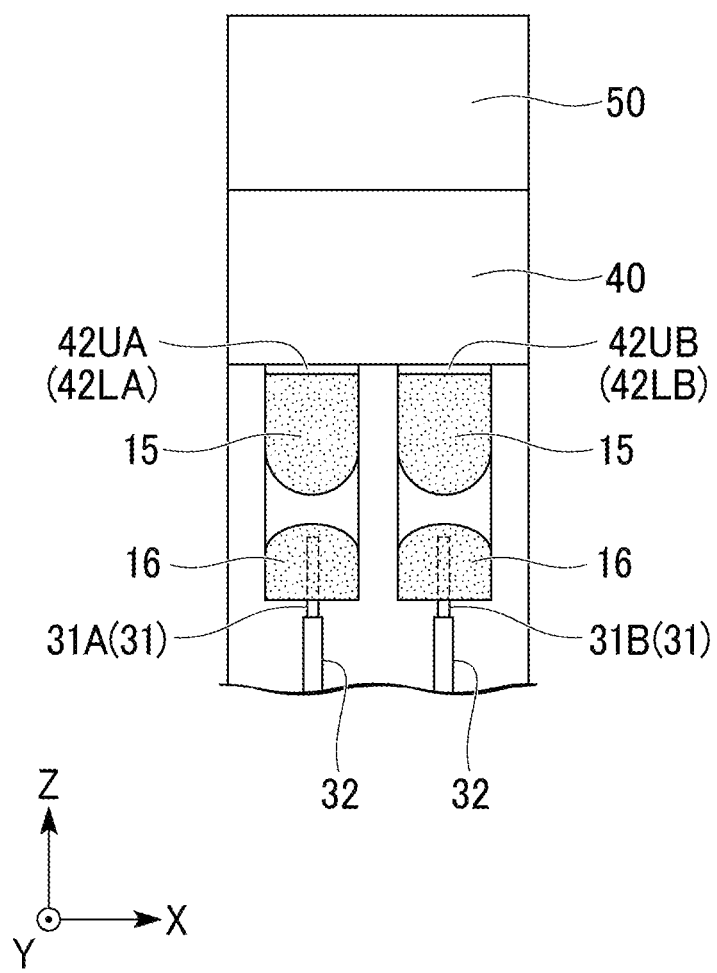
FIG. 3 is a view showing a part of the schematic configuration of the imaging module according to one or more embodiment of the invention and is a plan view when viewed from an upper surface of a substrate.

As shown in FIGS. 1 to 3, an imaging module 1 includes a substrate 10, a resin mold 20, a signal cable 30, a solid-state image sensing device 40 (image-sensing device), and a lens housing 50.

(Substrate)

The substrate 10 includes a substrate body 11 serves as an insulating member, wirings 12 (upper surface wirings 12U and lower surface wirings 12L which will be described later) that are formed on the substrate body 11. The substrate body 11 has an upper surface 11U (first surface) and a lower surface 11L (second surface) opposite to the upper surface 11U.

The upper surface wirings 12U are formed on the upper surface 11U. The lower surface wirings 12L are formed on the lower surface 11L. The wirings 12 each have a conductive wiring pattern on both surfaces of the upper surface 11U and the lower surface 11L.

The substrate body 11 (substrate 10) includes: a front-end face 11E (first end face) that faces an electrode surface 43 of the solid-state image sensing device 40; and a rear-end face 11F (second end face) opposite to the front-end face 11E. The substrate body 11 extends in a direction substantially orthogonal to the electrode surface 43 of the solid-state image sensing device 40. The rear-end face 11F is a surface adjacent to the signal cable 30.

The front-end face 11E may be in contact with the solid-state image sensing device 40 or may be spaced apart from the solid-state image sensing device 40 at a slight distance.

The substrate body 11 extends in a direction from the solid-state image sensing device 40 toward the signal cable 30, is located between the upper surface 11U and the lower surface 11L, and has a side surface 11S connected to the upper surface 11U and the lower surface 11L. The side surface 11S is exposed to the outside the substrate 10 and is not coated with the resin mold 20.

The substrate 10 has a through-hole interconnection 14 that penetrates through the substrate body 11 between the upper surface 11U and the lower surface 11L. The through-hole interconnection 14 electrically connects the upper surface wiring 12U and the lower surface wiring 12L.

An electrode terminal 12HU that forms part of the upper surface wiring 12U is formed on the upper surface 11U. An electrode terminals 12HL that forms part of the lower surface wiring 12L is formed on the lower surface 11L. That is, the electrode terminals are formed on both surfaces of the upper surface 11U and the lower surface 11L.

The electrode terminal 12HU is electrically connected via solder 15 to the image-sensing device electrode 42U (42) of the solid-state image sensing device 40 which will be described later. The electrode terminal 12HL is electrically connected via solder 15 the image-sensing device electrode 42L (42) of the solid-state image sensing device 40.

The solder 15 not only electrically connects the electrode terminal 12HU and the image-sensing device electrode 42U but also fixes the electrode terminal 12HU to the image-sensing device electrode 42U. Similarly, the solder 15 not only electrically connects the electrode terminal 12HL and the image-sensing device electrode 42L but also fixes the electrode terminal 12HL to the image-sensing device electrode 42L. Because of this, regardless of whether or not the front-end face 11E is in contact with the solid-state image sensing device 40, the positions of the front-end face 11E and the electrode surface 43 are fixed, and the solid-state image sensing device 40 is fixed to the substrate body 11.

In one or more embodiments, the upper surface wiring 12U is formed only on one surface of the substrate body 11, that is, only on the upper surface 11U. The upper surface wiring 12U includes an internal conductor terminal 12I (cable terminal) and an external conductor terminal 12J (cable terminal). The internal conductor terminal 12I is electrically connected to an internal conductor 31 of the signal cable 30 via solder 16 which will be described later. The external conductor terminal 12J is electrically connected to an external conductor 33 of the signal cable 30 via solder 17.

(Solid-State Image Sensing Device and Lens Housing)

The solid-state image sensing device 40 has a light-receiving face 41 and the electrode surface 43 on the opposite side of the light-receiving face 41 and includes four image-sensing device electrodes 42 provided on the electrode surface 43.

Specifically, as shown in FIGS. 2 and 3, the four image-sensing device electrodes 42 are the portions represented by reference numerals 42UA (42U), 42UB (42U), 42LA (42L), and 42LB (42L).

As shown in FIG. 2, the image-sensing device electrodes 42U (42UA, 42UB) and 42L (42LA, 42LB) are provided on the electrode surface 43 so as to be located above and below in the Y direction.

As shown in FIG. 3, the image-sensing device electrodes 42UA and 42UB are arranged so as to adjacent to each other in the X direction.

Note that, in the Y direction of FIG. 3, the image-sensing device electrode 42LA is disposed so as to overlap the image-sensing device electrode 42UA, and the image-sensing device electrode 42LB is disposed so as to overlap the image-sensing device electrode 42UB (i.e., arrangement of the image-sensing device electrodes 42U and 42L shown in FIG. 2).

The region between two of the image-sensing device electrodes 42U and 42L which are adjacent to each other in the Y direction is a central region R of the electrode surface 43. The substrate 10 is fixed to the electrode surface 43 by the solder 15 such that the front-end face 11E of the substrate body 11 is located at the central region R.

The electrode surface 43 has: corners 43U each of which is the starting point of the ridge line that determines the outer shape of a first resin portion 20U; and corners 43L each of which is the starting point of the ridge line that determines the outer shape of a second resin portion 20L.

In a state in which the front-end face 11E of the substrate 10 is disposed so as to face the central region R of the electrode surface 43 of the solid-state image sensing device 40, the image-sensing device electrode 42U has a surface parallel to the direction substantially orthogonal to the electrode terminal 12HU, and the image-sensing device electrode 42L has a surface parallel to the direction substantially orthogonal to the electrode terminal 12HL. In this configuration, the solder 15 connects the image-sensing device electrode 42U and the electrode terminal 12HU which are substantially orthogonal to each other, and connects the image-sensing device electrode 42L and the electrode terminal 12HL which are substantially orthogonal to each other. That is, the solder 15 not only electrically connects the image-sensing device electrode 42 and the electrode terminals 12HU, HL but also fixes the front-end face 11E of the substrate 10 to the electrode surface 43.

The lens housing 50 is connected to the light-receiving face 41, and a lens unit such as an object lens is mounted on the lens housing 50. As the solid-state image sensing device 40, for example, a CMOS (complementary metal oxide semiconductor) is used.

(Signal Cable)

Figure 4:
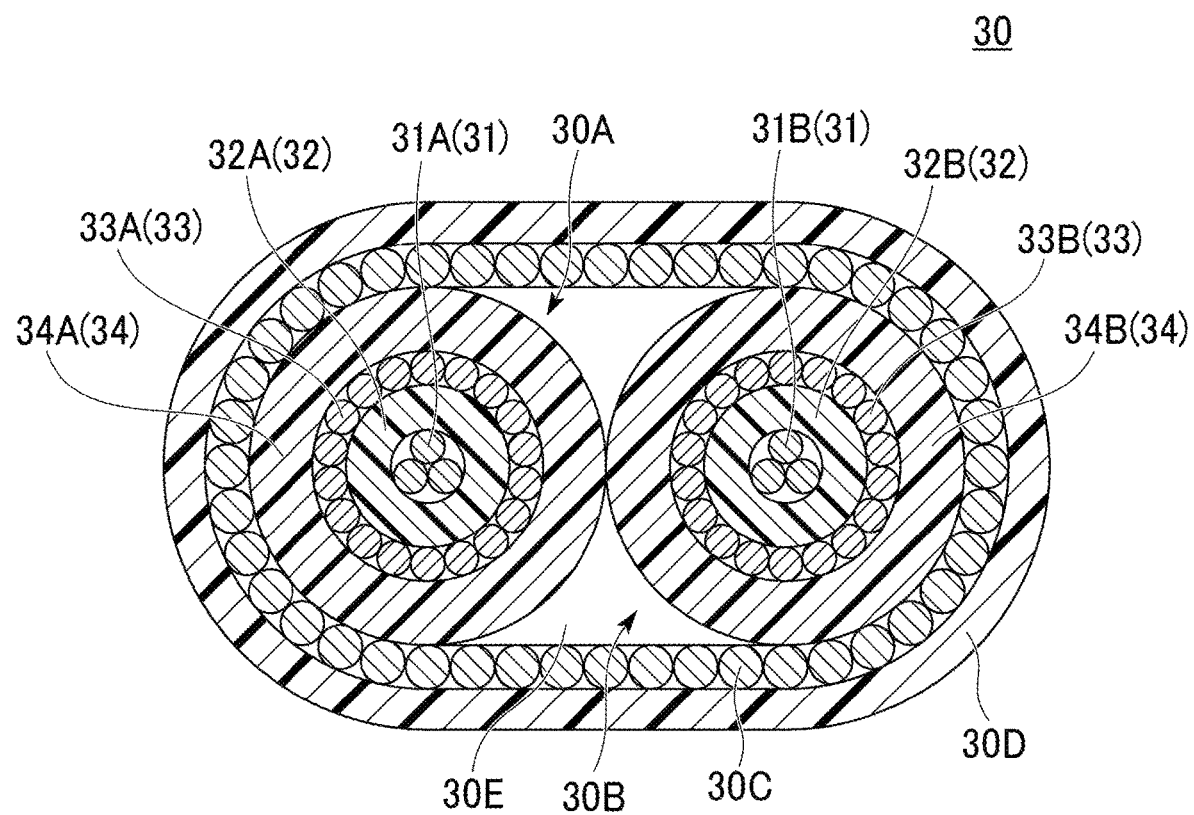
FIG. 4 is a cross-sectional view showing a signal cable the imaging module according to one or more embodiments of the invention.

FIG. 4 a cross-sectional view showing the signal cable 30 of the imaging module according to one or more embodiments of the invention.

The signal cable 30 includes two coaxial cables (a first coaxial cable 30A and a second coaxial cable 30B), a shield conductor 30C that surrounds the first coaxial cable 30A and the second coaxial cable 30B, and an outer coating 30D that surrounds the shield conductor 30C. A gap between the first coaxial cable 30A and the second coaxial cable 30B is filled with an insulating member 30E inside the shield conductor 30C. The signal cable 30 having the above-described configuration is provided on the upper surface 11U of the substrate 10 in one or more embodiments.

Each of the coaxial cables 30A and 30B includes an internal conductor 31 (conductor, 31A, 31B), an internal insulator 32 (32A, 32B), an external conductor 33 (conductor, 33A, 33B) that is located outside the internal conductor 31, and an external insulator 34 (34A, 34B). For example, the internal conductor 31 is used as a signal line that supplies a signal to the solid-state image sensing device 40, and the external conductor 33 is used as a power supply line that supplies electric power to the solid-state image sensing device 40.

The internal conductor 31 (31A, 31B) is electrically connected to the internal conductor terminal 12I of the substrate 10. The external conductor 33 (33A, 33B) is electrically connected to the external conductor terminal 12J of the substrate 10.

The shield conductor 30C and the outer coating 30D surrounds the first coaxial cable 30A and the second coaxial cable 30B over the entirety of the signal cable 30 but are removed at the region close to the substrate 10, and the first coaxial cable 30A and the second coaxial cable 30B are exposed from the shield conductor 30C and the outer coating 30D. The first coaxial cable 30A and the second coaxial cable 30B which are exposed are coated with the resin mold 20. Furthermore, as shown in FIGS. 1 and 2, the external conductor 33 and the internal conductor 31 which constitute each of the first coaxial cable 30A and the second coaxial cable 30B are exposed corresponding to a wiring pattern of the substrate 10 and are electrically connected to the wirings 12 by the solders 16 and 17.

Particularly, at the portions at which the first coaxial cable 30A and the second coaxial cable 30B are exposed, the shield conductor 30C and the outer coating 30D are removed and therefore outer coating end 35U and 35L shown in FIGS. 1 and 2 are formed. The outer coating end 35U corresponds to the end point of the ridge line that determines the outer shape of the first resin portion 20U. The outer coating end 35L corresponds to the end point of the ridge line that determines the outer shape of the second resin portion 20L.

(Wiring Pattern of Wiring 12 Formed on Substrate 10)

Figure 5A:
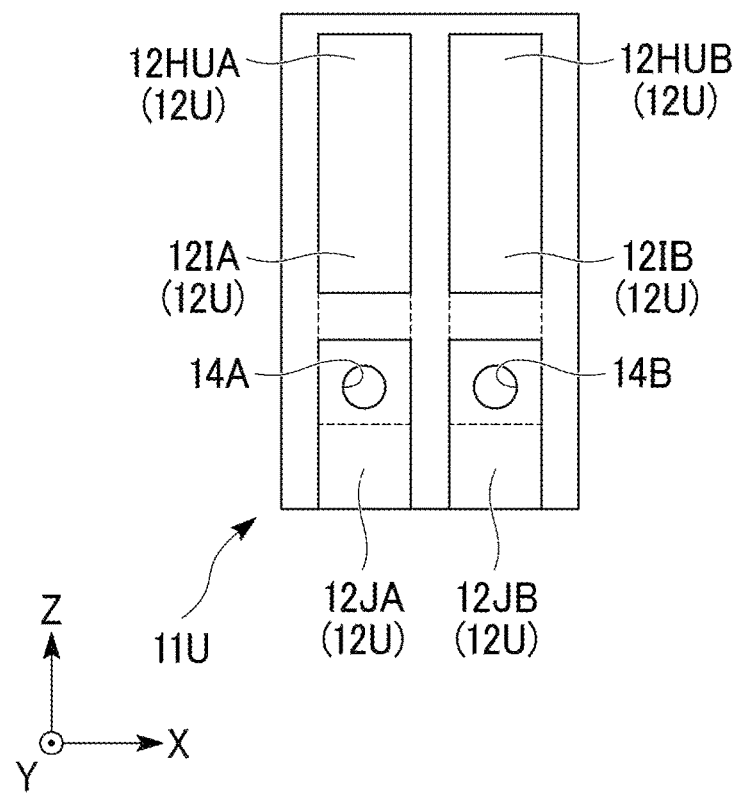
FIG. 5A is a view showing a wiring pattern of an upper surface wiring formed on an upper surface of the substrate of the imaging module according to one or more embodiments of the invention and is a view for explaining a connection structure of a solid-state image sensing device and the signal cable.
Figure 5B:
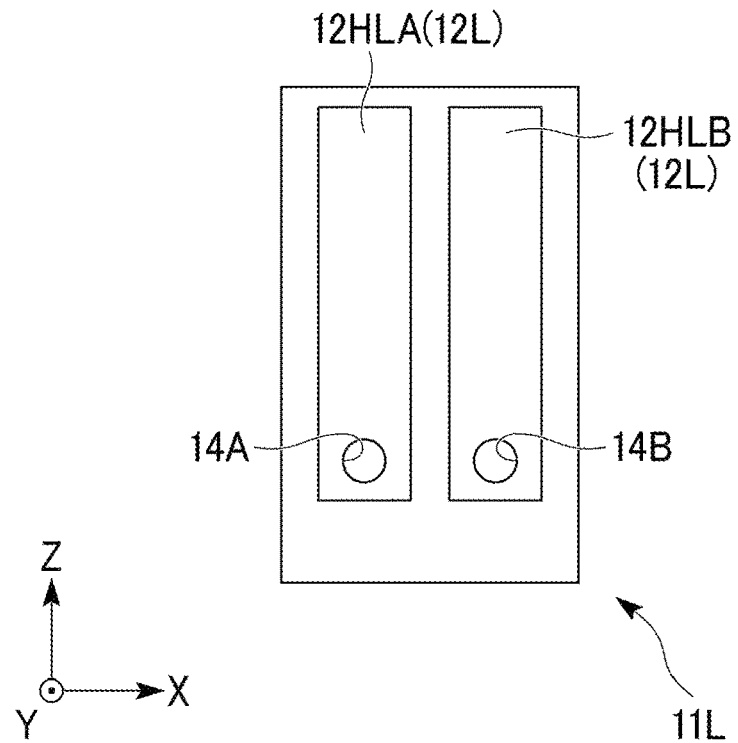
FIG. 5B is a view showing a wiring pattern of an upper surface wiring formed on a lower surface of the substrate of the imaging module according to one or more embodiments of the invention and is a view for explaining a connection structure of a solid-state image sensing device and the signal cable.

FIGS. 5A and 5B are views showing wiring patterns formed on the substrate 10. FIG. 5A shows a wiring pattern of the upper surface wiring 12U formed on the upper surface 11U of the substrate body 11. FIG. 5B shows a wiring pattern of the lower surface wiring 12L formed on the lower surface 11L of the substrate body 11. Note that, FIG. 5B is not a bottom view showing the lower surface 11L but is a projection view when viewed from the upper surface 11U shown in FIG. 5A. Therefore, a broken-line portion shown in FIG. 5A corresponds to a solid-line portion shown in FIG. 5B.

Reference numeral 12JA corresponds to the external conductor terminal 12J and is a terminal to which the external conductor 33A of the first coaxial cable 30A is connected via the solder 17. Hereinbelow, this is referred to as an external conductor terminal 12JA. Reference numeral 12JB corresponds to the external conductor terminal 12J and is a terminal to which the external conductor 33B of the second coaxial cable 30B is connected via the solder 17. Hereinbelow, this is referred to as an external conductor terminal 12JB.

Reference numeral 12IA corresponds to the internal conductor terminal 12I and is a terminal to which the internal conductor 31A of the first coaxial cable 30A is connected via the solder 16. Hereinbelow, this is referred to as an internal conductor terminal 12IA. Reference numeral 12IB corresponds to the internal conductor terminal 12I and is a terminal to which the internal conductor 31B of the second coaxial cable 30B is connected via the solder 16. Hereinbelow, this is referred to as an internal conductor terminal 12IB.

Reference numeral 12HUA is a terminal that corresponds to the electrode terminal 12HU and is hereinbelow referred to as an electrode terminal 12HUA. Reference numeral 12HUB is a terminal that corresponds to the electrode terminal 12HU and is hereinbelow referred to as an electrode terminal 12HUB.

Reference numeral 12HLA is a terminal that corresponds to the electrode terminal 12HL and is hereinbelow referred to as an electrode terminal 12HLA. Reference numeral 12HLB is a terminal that corresponds to the electrode terminal 12HL and is hereinbelow referred to as an electrode terminal 12HLB. Reference numerals 14A and 14B correspond to the through-hole interconnection 14 and is hereinbelow referred to as through-hole interconnections 14A and 14B.

As shown in FIG. 5A, the external conductor terminal 12JA is electrically connected to the through-hole interconnection 14A. Similarly, the external conductor terminal 12JB is electrically connected to the through-hole interconnection 14B. Moreover, the internal conductor terminal 12IA is electrically connected to the electrode terminal 12HUA. Similarly, the internal conductor terminal 12IB is electrically connected to the electrode terminal 12HUB.

The external conductor terminals 12JA and 12JB, the internal conductor terminals 12IA and 12IB, and the electrode terminals 12HUA and 12HUB can be collectively formed by patterning using a known photolithographic technique or the like.

As shown in FIG. 5B, the through-hole interconnection 14A is electrically connected to the electrode terminal 12HLA. Similarly, the through-hole interconnection 14B is electrically connected to the electrode terminal 12HLB. This means that the external conductor terminal 12JA formed on the upper surface 11U is electrically connected to the electrode terminal 12HLA formed on the lower surface 11L via the through-hole interconnection 14A. Additionally, the external conductor terminal 12JB formed on the upper surface 11U is electrically connected to the electrode terminal 12HLB formed on the lower surface 11L via the through-hole interconnection 14B.

The electrode terminals 12HLA and 12HLB can be collectively formed by patterning using a known photolithographic technique or the like.

Furthermore, the through-hole interconnections 14A and 14B can also be formed by a known method.

In FIGS. 5A and 5B, although the wiring 12 (external conductor terminal, internal conductor terminal, electrode terminal) has a configuration in which the two-line wiring pattern extending straight in the extending direction of the substrate body 11 is formed on each of the upper surface 11U and the lower surface 11L, the invention is not limited to the above-described linear wiring pattern. The wiring 12 may has a cross pattern such that the first line of the wiring provided on the upper surface 11U is connected to the second line of the wiring provided on the lower surface 11L and the second line of the wiring provided on the upper surface 11U is connected to the first line of the wiring provided on the lower surface 11L.

Next, an electrical connection structure of the first coaxial cable 30A and the second coaxial cable 30B with respect to the image-sensing device electrode 42 will be described.

As shown in FIGS. 2, 3, and 5A, the internal conductor 31A of the first coaxial cable 30A is electrically connected to the internal conductor terminal 12IA via the solder 16. In addition, the internal conductor 31B of the second coaxial cable 30B is electrically connected to the internal conductor terminal 12IB via the solder 16.

Consequently, the internal conductor 31A is connected to the image-sensing device electrode 42U (42UA) via the internal conductor terminal 12IA and the electrode terminal 12HUA, and the internal conductor 31B is connected to the image-sensing device electrode 42U (42UB) via the internal conductor terminal 12IB and the electrode terminal 12HUB.

Here, the image-sensing device electrode 42UA is one electrode of two image-sensing device electrodes 42U, that is, an electrode connected to the internal conductor 31A of the first coaxial cable 30A. The image-sensing device electrode 42UB is the other electrode of the two image-sensing device electrodes 42U, that is, an electrode connected to the internal conductor 31B of the second coaxial cable 30B. The image-sensing device electrodes 42UA and 42UB are arranged side by side in the X direction shown in FIGS. 1 and 2.

As shown in FIGS. 2, 3, 5A, and 5B, the external conductor 33A of the first coaxial cable 30A is electrically connected to the external conductor terminal 12JA via the solder 17. Furthermore, the external conductor 33B of the second coaxial cable 30B is electrically connected to the external conductor terminal 12JB via the solder 17. The external conductor terminal 12JA reaches the lower surface 11L via the through-hole interconnection 14A and is connected to the electrode terminal 12HLA. The external conductor terminal 12JB reaches the lower surface 11L via the through-hole interconnection 14B and is connected to the electrode terminal 12HLB.

Therefore, the external conductor 33A is connected to the image-sensing device electrode 42L (42LA) via the external conductor terminal 12JA and the electrode terminal 12HLA, and the external conductor 33B is connected to the image-sensing device electrode 42L (42LB) via the external conductor terminal 12JB and the electrode terminal 12HLB. Here, the image-sensing device electrode 42LA is one electrode of two image-sensing device electrodes 42L, that is, an electrode connected to the external conductor 33A of the first coaxial cable 30A. The image-sensing device electrode 42LB is the other electrode of the two image-sensing device electrodes 42L, that is, an electrode connected to the external conductor 33B of the second coaxial cable 30B. The image-sensing device electrodes 42LA and 42LB are arranged side by side in the X direction shown in FIGS. 1 and 2.

(Resin Mold)

The resin mold 20 is formed of a resin material having electrical insulation, for example, epoxy resin or the like and includes the first resin portion 20U coating the upper surface 11U and the second resin portion 20L coating the lower surface 11L. That is, the resin mold 20 coats both surfaces of the upper surface 11U and the lower surface 11L. Furthermore, the resin mold 20 coats not only the upper surface 11U and the lower surface 11L but also the rear-end face 11F. Particularly, the resin mold 20 does not coat the side surface 11S.

For example, FIGS. 1 and 2 show the configuration in which the rear-end face 11F is coated with the resin mold 20; however, the entirety of the rear-end face 11F is not coated with the resin mold 20 and the rear-end face 11F may be partially exposed. Furthermore, the entirety of the rear-end face 11F may be exposed.

The first resin portion 20U extends from the solid-state image sensing device 40 to the signal cable 30 so as to coat the entirety of the image-sensing device electrodes 42U, the solders 15, 16, and 17, the upper surface wiring 12U (internal conductor terminal 12I and external conductor terminal 12J), the internal conductor 31, and the external conductor 33 on the electrode surface 43 and the upper surface 11U of the substrate body 11. The first resin portion 20U is formed in a fillet shape having a curved surface F extending from the corner 43U of the electrode surface 43 of the solid-state image sensing device 40 to the outer coating end 35U of the signal cable 30. The curved surface F has a shape (fillet shape) that is depressed with respect to the straight line connecting the corner 43U and the outer coating end 35U in a recessed shape.

Here, the outer coating end 35U is the portion (the end of the outer coating 30D) that is formed by removing the outer coating 30D of the signal cable 30 and is a part of the outer coating 30D.

In the XY cross-section of FIG. 1, the first resin portion 20U has an arch shape or a substantially U-shape in cross-section configuration.

The second resin portion 20L extends from the solid-state image sensing device 40 to the signal cable 30 so as to coat the entirety of the image-sensing device electrodes 42L and the lower surface wiring 12L on the electrode surface 43 and the lower surface 11L of the substrate body 11. The second resin portion 20L is formed in a fillet shape having a curved surface F extending from the corner 43L of the electrode surface 43 of the solid-state image sensing device 40 to the outer coating end 35L of the signal cable 30. The curved surface F has a shape (fillet shape) that is depressed with respect to the straight line connecting the corner 43L and the outer coating end 35L. In other words, the external form line of the second resin portion 20L is a curved line connecting the corner 43L and the outer coating end 35L.

Here, similar to the outer coating end 35U, the outer coating end 35L is the portion (the end of the outer coating 30D) that is formed by removing the outer coating 30D of the signal cable 30 and is a part of the outer coating 30D.

In the XY cross-section of FIG. 1, the second resin portion 20L has a substantially arch shape or a U-shape in cross-section configuration.

In FIGS. 1 and 2, the resin mold 20 and the signal cable 30 are disposed inside the outline of the solid-state image sensing device 40 (external form line) on a plane of projection of the solid-state image sensing device 40 when viewed in a direction from the solid-state image sensing device 40 to the signal cable 30. Particularly, the resin mold 20 and the signal cable 30 does not partially protrude to the outside from the outline of the solid-state image sensing device 40 on the plane of projection.

(Method of Forming Resin Mold)

A method of forming the resin mold 20 including the first resin portion 20U and the second resin portion 20L will be described. A step of forming the resin mold 20 is carried out after completion of electrical connection of the substrate 10, the solid-state image sensing device 40, and the signal cable 30 by the solders 15, 16, and 17.

Moreover, thermosetting resin or ultraviolet curable resin is used as the type of resin material forming the resin mold 20, and a method of forming the resin mold 20 differs depending on the type of the resin material.

(Case of Forming Resin Mold Using Thermosetting Resin)

Firstly, resin material in a liquid state which is to be the first resin portion 20U is applied onto the upper surface 11U. Since the resin material in a liquid state applied onto the upper surface 11U has flowability before the first resin portion 20U is thermally-cured, the resin material in a liquid state spreads in a wet state on the entire surface of the upper surface 11U while maintaining a state in which the solders 15, 16, and 17, the upper surface wiring 12U, the lower surface wiring 12L, the internal conductor 31, the external conductor 33, and the upper surface 11U are coated with the resin material in a liquid state.

Furthermore, the resin material in a liquid state comes into contact with the outer coating 30D of the signal cable 30 so as to form the fillet shape having the curved surface F extending from the corner 43U of the electrode surface 43 to the outer coating end 35U of the signal cable 30 due to the action of surface tension while flowing on the upper surface 11U. The outer coating 30D is formed of fluorine-based resin material and has a high degree of liquid repellency to the resin material in a liquid state. Consequently, the resin material does not flow such that the coating amount of the resin material with respect to an outer coating surface 30DS of the outer coating 30D increases. In other words, even where the outer coating surface 30DS is slightly coated with the resin material near the outer coating end 35U, the surface area on which the outer coating surface 30DS is coated with the resin material is limited. The above-described behavior in which the resin material in a liquid state flows stops due to the resin material coming into contact with the outer coating end 35U.

Next, resin material in a liquid state which is to be the second resin portion 20L is applied onto the lower surface 11L without heat-curing the resin material that was applied onto the upper surface 11U. Since the resin material in a liquid state applied onto the lower surface 11L has flowability before the second resin portion 20L is thermally-cured, the resin material in a liquid state spreads in a wet state on the entire surface of the lower surface 11L while maintaining a state in which the lower surface wiring 12L and the lower surface 11L are coated with the resin material in a liquid state.

Furthermore, the resin material in a liquid state comes into contact with the first resin portion 20U that was applied onto the upper surface 11U in advance so as to form the fillet shape having the curved surface F extending from the corner 43L of the electrode surface 43 to the outer coating end 35L of the signal cable 30 due to the action of surface tension while flowing on the lower surface 11L, and comes into contact with the outer coating 30D of the signal cable 30. Moreover, as described above, since the outer coating 30D has liquid repellency to the resin material in a liquid state, the resin material does not flow such that the coating amount of the resin material with respect to the outer coating surface 30DS of the outer coating 30D increases. In other words, even where the outer coating surface 30DS is slightly coated with the resin material near the outer coating end 35L, the surface area on which the outer coating surface 30DS is coated with the resin material is limited. The above-described behavior in which the resin material in a liquid state flows stops due to the resin material coming into contact with the outer coating end 35L.

Thereafter, a heat-curing step is carried out, and therefore the resin materials in a liquid state which were applied onto the upper surface 11U and the lower surface 11L are integrally cured by heat-curing treatment. As a result, the resin mold 20 having the first resin portion 20U and the second resin portion 20L which are integrated into a body is obtained.

In other cases, in the case of using thermosetting resin, the order of applying the resin onto the upper surface 11U and the lower surface 11L is not limited. After applying resin onto the lower surface 11L, resin may be applied onto the upper surface 11U. Even in this case, the resin materials in a liquid state which were applied onto the upper surface 11U and the lower surface 11L are integrally cured by heat-curing treatment.

(Case of Forming Resin Mold Using Ultraviolet Curable Resin)

Firstly, in a similar way to the case forming the resin mold using the aforementioned thermosetting resin, resin material in a liquid state is applied onto the entire surface of the upper surface 11U so as to have a fillet shape. The behavior in which the resin material in a liquid state flows stops due to the resin material coming into contact with the outer coating end 35U. Thereafter, the first resin portion 20U is formed by irradiating the resin material with ultraviolet light.

Next, resin material in a liquid state is applied onto the entire surface of the lower surface 11L so as to have a fillet shape. The resin material comes into contact with the first resin portion 20U while flowing on the lower surface 11L. The behavior in which the resin material in a liquid state flows stops due to the resin material coming into contact with the outer coating end 35L. Thereafter, the second resin portion 20L is formed by irradiating the resin material with ultraviolet light. As a result, the resin mold 20 having the first resin portion 20U and the second resin portion 20L which are integrated into a body is obtained.

In other cases, in the case of using ultraviolet curable resin, the order of forming the first resin portion 20U and the second resin portion 20L is not limited. After the second resin portion 20L is formed, the first resin portion 20U may be formed.

Note that, even in the case of using the above-mentioned thermosetting resin or ultraviolet curable resin, in the process in which the substrate 10 is coated with the resin material while the resin material flows on the surface (upper surface 11U and lower surface 11L) of the substrate 10, the resin material in a liquid state may reach the rear-end face 11F or may not reach the rear-end face 11F. Whether or not the rear-end face 11F is coated with the resin material in a liquid state, whether or not the rear-end face 11F is partially coated therewith, and whether or not the rear-end face is entirely coated therewith depends on variation in the condition such as the degree of viscosity or the like of the resin material in a liquid state before heat-curing.

In the method of forming the above-described resin mold 20, since the resin mold 20 can be formed by applying and curing the resin material in a liquid state, a die for forming the resin mold 20 is not necessary.

In the imaging module 1 according to one or more embodiments, since the first resin portion 20U and the second resin portion 20L are formed, it is possible to increase the joint strength between the image-sensing device electrodes 42 and the wirings 12 due to the solder 15.

Particularly, in the configuration in which the front-end face 11E is disposed on the electrode surface 43 in a T-shape as shown in FIG. 2 and is fixed thereto by the solder 15, stress concentration easily occurs at the connection portion between the electrode terminal 12HU (12HL) and the image-sensing device electrode 42U (42L), a higher strength is required at this portion.

In contrast, the connection portion between the electrode terminal 12HU (12HL) and the image-sensing device electrodes 42U (42L) is coated with the first resin portion 20U and the second resin portion 20L, it is possible to improve the strength of the aforementioned T-shaped connection structure.

Furthermore, the image-sensing device electrodes 42 of the solid-state image sensing device 40 are electrode pads formed on a semiconductor device, are portions which are easily peeled off, and need to have a high degree of reliability in electrical connection. With respect to the above-described easy peeled off portions, it is possible to improve the joint strength between wirings or electrodes and terminals which are formed on the substrate having the wirings 12.

In addition, since the first resin portion 20U are formed on the electrode surface 43 and the upper surface 11U, it is possible to increase the joint strength of the entirety of the image-sensing device electrodes 42U, the solders 15, 16, and 17, the upper surface wiring 12U (internal conductor terminal 12I and external conductor terminal 12J), the internal conductor 31, and the external conductor 33.

Similarly, since the second resin portion 20L is formed on the electrode surface 43 and the lower surface 11L, it is possible to increase the joint strength between the image-sensing device electrode 42L and the lower surface wiring 12L.

Furthermore, since the resin mold 20 is formed on both surfaces of the substrate body 11, it is possible to further increase the strength of the substrate body 11.

Moreover, since a plurality of the image-sensing device electrodes 42, the wirings 12, the solders 15, 16, and 17, the internal conductors 31, and the external conductors 33 are coated with the resin mold 20 on the electrode surface 43, the upper surface 11U, and the lower surface 11L, it is possible to ensure electrical insulation.

Additionally, the resin mold 20 and the signal cable 30 are disposed inside the outline of the solid-state image sensing device 40 (external form line) on a plane of projection of the solid-state image sensing device 40 when viewed in a direction from the solid-state image sensing device 40 to the signal cable 30, the size of the imaging module 1 on the XY plane can be less than or equal to the size of the solid-state image sensing device 40. For this reason, it is possible to ensure reduction in diameter of the imaging module 1.

Furthermore, since the resin mold 20 is not formed on the side surface 11S, the thicknesses of the first resin portion 20U and the second resin portion 20L can be maintained, and it is possible to synergistically obtain the effects of maintaining the joint strength and ensuring the electrical insulation.

Hereinbelow, the above effects will be particularly described with reference to the case in which resin material in a liquid state forming the second resin portion 20L flows on the side surface 11S in a state in which the first resin portion 20U is formed on the side surface 11S.

In this case, when the resin material in a liquid state forming the second resin portion 20L comes into contact with the first resin portion 20U, the resin material in a liquid state flows from the lower surface 11L to the side surface 11S so as to coat the side surface 11S in accordance with the contact between the resin material in a liquid state and the first resin portion 20U (pump-priming effect). As a result, the amount of the resin material of the lower surface 11L is reduced, and the thickness of the second resin portion 20L decreases. Furthermore, in accordance with reduction in the thickness of the second resin portion 20L, the strength thereof is lowered, and the electrical insulation thereof is degraded.

In contrast, since the side surface 11S is exposed to the outside of the substrate 10 and is not coated with the resin mold 20, the amount of the resin material of the lower surface 11L is not reduced, the strength thereof is not lowered, and also the electrical insulation thereof is not degraded. Consequently, the thickness of the second resin portion 20L does not decrease, the strength thereof is not lowered, and the electrical insulation thereof is not degraded.

Furthermore, since the resin mold 20 is not formed on the side surface 11S, the size of the imaging module 1 in the X direction of FIGS. 1 and 2 does not increase. As a result, it is possible to achieve reduction in diameter of the imaging module 1.

While embodiments of the invention have been described and illustrated above, it should be understood that these are exemplary examples of the invention and are not to be considered as limiting. Additions, omissions, substitutions, and other modifications can be made without departing from the scope of the invention. Accordingly, the invention is not to be considered as being limited by the foregoing description, and is only limited by the scope of the appended claims.

Modified Example 1

Although the resin mold 20 is formed on both surfaces of the upper surface 11U and the lower surface 11L in one or more embodiments, it is only necessary that at least one of the upper surface 11U and the lower surface 11L is coated with the resin mold 20. However, in order to obtain the electrical insulation, the resin mold 20 should be formed on the surface on which the solders 15, 16, and 17, the wirings 12, the internal conductor 31, and the external conductor 33 are arranged.

In FIGS. 1 and 2, although the resin mold 20 is formed on the substrate 10 so as to coat the surfaces of the solders 15, 16, and 17, and the wirings 12; however, the invention is not limited to this configuration. A configuration may be adopted in which a resist that coats at least one of surfaces of the solder and the wiring is formed therein and the surface of the resist is coated with the resin mold 20.

Additionally, not only the configuration having the resist formed on the lower layer of the resin mold 20 but also a configuration having a stress relief layer that releases stress to be generated among the solders 15, 16, and 17, the wirings 12 and the resin mold 20 may be adopted.

Furthermore, as long as a sufficient space exists above the lower surface 11L of the substrate body 11, a capacitor (bypass capacitor) may be provided between the electrode terminal 12HLA and the electrode terminal 12HLB. In this configuration, the capacitor is coated with the second resin portion 20L of the resin mold 20.

In FIG. 2, although the first coaxial cable 30A and the second coaxial cable 30B are arranged only on the upper surface 11U and the internal conductor terminal 12I and the external conductor terminal 12J of each coaxial cable is formed on the upper surface 11U; however, the invention is not limited to this configuration. Instead of the upper surface 11U, the first coaxial cable 30A and the second coaxial cable 30B may be arranged only on the lower surface 11L, the internal conductor terminal 12I and the external conductor terminal 12J of each coaxial cable may be formed on the lower surface 11L. Furthermore, a coaxial cable may be arranged on each of the upper surface 11U and the lower surface 11L, and the internal conductor terminal 12I and the external conductor terminal 12J of each coaxial cable may be formed thereon.

Modified Example 2

Although the second resin portion 20L has the fillet shape in one or more embodiments, the invention is not limited to this configuration.

In the example shown in FIG. 2, the second resin portion 20L coats a substrate lower end 10L at which the lower surface 11L intersects with the rear-end face 11F, the second resin portion 20L may not coat the substrate lower end 10L. For example, the second resin portion 20L may be formed in a fillet shape having a curved surface extending from the corner 43L of the electrode surface 43 to the substrate lower end 10L. In other words, the external form line of the second resin portion 20L may be a curved line connecting the corner 43L and the substrate lower end 10L.

The shape of the curved surface F is adjustable by the degree of viscosity of the resin material in a liquid state which forms the resin mold 20 and is before heat-cured. For example, in the case in which the viscosity of the pre-heat-cured resin material in a liquid state is low, since the resin material in a liquid state easily spreads in a wet state on the substrate body 11, the flowability of the resin material in a liquid state is high, and there is a tendency that the resin mold 20 becomes thinner.

In contrast, in the case in which the viscosity of the pre-heat-cured resin material in a liquid state is high, although the resin material in a liquid state is difficult to spread in a wet state on the substrate body 11 as compared with the case in which the degree of viscosity is low, there is an advantage in that the resin mold 20 can be thicker. Moreover, the thickness of the portion of the resin mold 20 which has the fillet shape become larger. Consequently, the strength between the electrode terminal 12HU (HL) and the image-sensing device electrode 42U (42L) due to the solder 15 sufficiently increases.

As stated above, it is possible to form the resin mold 20 so as to have a desired thickness by adjusting the degree of viscosity of the resin material in a liquid state before heat-curing.

Additionally, by adjusting liquid-repellency or liquid-affinity of the surface of the portion to which the resin material is applied, with respect to the resin material in a liquid state, it is possible to adjust the configuration of the curved surface F.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

REFERENCE SIGNS LIST

1 . . . imaging module
10 . . . substrate
10L . . . substrate lower end
11 . . . substrate body
11E . . . front-end face (first end face)
11F . . . rear-end face (second end face)
11L . . . lower surface (second surface)
11S . . . side surface
11U . . . upper surface (first surface)
12 . . . wiring
12HL, 12HLA, 12HLB, 12HU, 12HUA, 12HUB . . . electrode terminal
12I, 12IA, 12IB . . . internal conductor terminal
12J, 12JA, 12JB . . . external conductor terminal
12L . . . lower surface wiring
12U . . . upper surface wiring
14, 14A, 14B . . . through-hole interconnection
15, 16, 17 . . . solder
20 . . . resin mold
20L . . . second resin portion
20U . . . first resin portion
30 . . . signal cable
30A . . . first coaxial cable (coaxial cable)
30B . . . second coaxial cable (coaxial cable)
30C . . . shield conductor
30D . . . outer coating
30DS . . . outer coating surface
30E . . . insulating member 31, 31A, 31B . . . internal conductor
32, 32A, 32B . . . internal insulator
33, 33A, 33B . . . external conductor
34, 34A, 34B . . . external insulator
35L, 35U . . . outer coating end
40 . . . solid-state image sensing device (image-sensing device)
41 . . . light-receiving face
42, 42L, 42LA, 42LB, 42U, 42UA, 42UB . . . image-sensing device electrode
43 . . . electrode surface
43L, 43U . . . corner
50 . . . lens housing
F . . . curved surface
R . . . central region

The invention claimed is:

1. An imaging module comprising: an image-sensing device comprising: a light-receiving face; an electrode surface located on an opposite side of the light-receiving face; and image-sensing device electrodes on the electrode surface; a substrate comprising: a first surface; a second surface opposite to the first surface; a first end face that faces the electrode surface between two image-sensing device electrodes adjacent to each other; and wiring on the first surface and the second surface, wherein the wiring is an insulating member and comprises an electrode terminal and a cable terminal, and at least one of the image-sensing device electrodes is electrically connected to the electrode terminal via solder; a signal cable comprising a conductor electrically connected to the image-sensing device via the wiring and to the cable terminal via the solder; and a resin mold that coats the electrode surface, the cable terminal, the conductor, and at least one of the first surface and the second surface on the substrate, on a plane of projection of the image-sensing device when viewed in a direction from the image-sensing device to the signal cable, the substrate, the resin mold, and the signal cable are disposed inside an outline of the image-sensing device.

2. The imaging module according to claim 1, wherein the substrate further comprises a side surface that is connected to the first surface and the second surface via a corner,
the side surface extends in a direction from the image-sensing device to the signal cable, and
the side surface is not coated with the resin mold.

3. The imaging module according to claim 1, wherein the substrate further comprises a second end face opposite to the first end face, and
the resin mold coats the second end face.

4. The imaging module according to claim 3, wherein the resin mold coats both surfaces of the first surface and the second surface,
the resin mold comprises a first resin portion that coats the first surface and a second resin portion that coats the second surface, and
the first resin portion is connected to the second resin portion on the second end face.

5. The imaging module according to claim 1, wherein the resin mold is formed in a fillet shape comprising a curved surface extending from a corner of the electrode surface to an outer coating end of the signal cable.

6. The imaging module according to claim 1, wherein the signal cable is a coaxial cable comprising an internal conductor and an external conductor outside the internal conductor,
the cable terminal of the substrate comprises:
an internal conductor terminal that is electrically connected to the internal conductor via the solder; and
an external conductor terminal electrically connected to the external conductor via the solder, and
the resin mold coats an entirety of the image-sensing device electrode, the internal conductor, the external conductor, the solder, the internal conductor terminal, and the external conductor terminal.

* * * * *